US012612375B2

(12) United States Patent
Mueller et al.

(10) Patent No.: US 12,612,375 B2
(45) Date of Patent: Apr. 28, 2026

(54) ANTIMICROBIAL AND ANTICANCER AGENTS

(71) Applicant: Persevere Therapeutics Inc., Chesterbrook, PA (US)

(72) Inventors: Thomas Mueller, Wolhusen (CH); Hanns Moehler, Maennedorf (CH); James C. Costin, Phoenixville, PA (US)

(73) Assignee: Persevere Therapeutics Inc., Chesterbrook, PA (US)

( * ) Notice: Subject to any disclaimer, the term of this patent is extended or adjusted under 35 U.S.C. 154(b) by 401 days.

(21) Appl. No.: 18/556,480

(22) PCT Filed: Apr. 28, 2022

(86) PCT No.: PCT/IB2022/053973
§ 371 (c)(1),
(2) Date: Oct. 20, 2023

(87) PCT Pub. No.: WO2022/229907
PCT Pub. Date: Nov. 3, 2022

(65) Prior Publication Data

US 2024/0199563 A1 Jun. 20, 2024

Related U.S. Application Data

(60) Provisional application No. 63/181,492, filed on Apr. 29, 2021.

(51) Int. Cl.
*C07D 291/06* (2006.01)
*A61K 31/549* (2006.01)
*A61K 45/06* (2006.01)
*A61K 47/10* (2017.01)
*A61P 31/04* (2006.01)
*A61P 35/00* (2006.01)

(52) U.S. Cl.
CPC .......... *C07D 291/06* (2013.01); *A61K 31/549* (2013.01); *A61K 45/06* (2013.01); *A61K 47/10* (2013.01); *A61P 31/04* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 3,202,657 | A | 8/1965 | Rudolf et al. |
| 9,241,943 | B2 | 1/2016 | Pfirrmann |
| 2015/0182534 | A1 | 7/2015 | Pfirrmann |

FOREIGN PATENT DOCUMENTS

| | | | |
|---|---|---|---|
| CN | 110776479 | A | 2/2020 |
| WO | 2020234828 | A1 | 11/2020 |

OTHER PUBLICATIONS

International Search Report issued for the International Application No. PCT/IB2022/053973 on Aug. 10, 2022, 3 pages.
Simplicio et al: "Prodrugs for amines", Molecules, MDPI AG, CH,vol. 13, No. 3, Jan. 1, 2008, pp. 519-547, XP002503564.
International Preliminary Report on Patentability and Written Opinion issued in PCT/IB2002/053973 dated Nov. 9, 2023, 9 pgs.
Chinese Office Action issued for corresponding Chinese Application No. 2022800319096 dated Jul. 24, 2025 (21 pages).

*Primary Examiner* — Sarah Pihonak
*Assistant Examiner* — Donna M Nestor
(74) *Attorney, Agent, or Firm* — ROTHWELL, FIGG, ERNST & MANBECK, P.C.

(57) ABSTRACT

Compounds of formula (I) useful as antineoplastic and antimicrobial agents are disclosed Compositions and methods of using antineoplastic and antimicrobial compounds are disclosed.

(I)

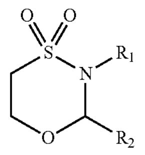

23 Claims, 9 Drawing Sheets

ANTIMICROBIAL AND ANTICANCER AGENTS

CROSS REFERENCE TO RELATED APPLICATION

This application is a 35 U.S.C. 371 National Phase Entry Application from PCT/IB2022/053973, filed Apr. 28, 2022, which claims the benefit of U.S. Provisional Application No. 63/181,492 filed on Apr. 29, 2021, the disclosures of which are incorporated herein in their entirety by reference.

FIELD OF THE INVENTION

The present invention relates to new compounds and uses thereof.

BACKGROUND

Many compounds are known, e.g., for treatment of cancers in patients or for treatment of microbial infections in patients.

There remains a need in the art for new compounds with more potent antineoplastic and antimicrobial activity, less toxicity and side effects, and less resistance to treatment by tumor or microbial cells.

SUMMARY OF THE INVENTION

In accordance with the present invention, new compounds and their uses are disclosed.

In one aspect, the present disclosure includes a compound selected from a compound of Formula I:

Formula I

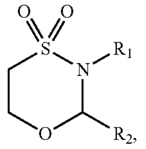

wherein $R_1$ is —CO-aryl or C1-C6 branched or unbranched alkyl and $R_2$ is H.

In one aspect, the present disclosure includes a compound selected from:

2289

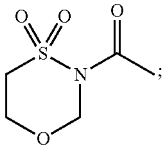

;

2293

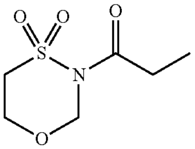

; or

-continued

2296

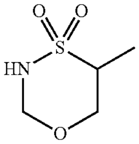

.

In one aspect, the present disclosure includes a pharmaceutical composition including a compound of the present disclosure.

In one aspect, the present disclosure includes an oral dosage form including a compound of the present disclosure.

In one aspect, the present disclosure includes a method of treating a subject by administering to said subject a compound, composition, or oral dosage form of the present disclosure.

In one aspect, the present disclosure includes a method of treating a subject suffering from cancer by administering to said subject a compound, composition, or oral dosage form of the present disclosure.

In one aspect, the present disclosure includes a method of treating tumor stem cells in a subject by administering to said subject a compound, composition, or oral dosage form of the present disclosure.

In one aspect, the present disclosure includes a method of treating a subject in need of anti-angiogenesis by administering to said subject a compound, composition, or oral dosage form of the present disclosure.

In one aspect, the present disclosure includes a method of treating a subject in need of anti-tubulogenesis by administering to said subject a compound, composition, or oral dosage form of the present disclosure.

In one aspect, the present disclosure includes a method of treating a subject suffering from a bacterial infection by administering to said subject a compound, composition, or oral dosage form of the present disclosure.

In one aspect, the present disclosure includes a method of treating a subject suffering from a viral infection by administering to said subject a compound, composition, or oral dosage form of the present disclosure.

In one aspect, the present disclosure includes a co-therapeutic composition or regimen including taurolidine and/or taurultam in combination with at least one compound, pharmaceutical composition, or oral dosage form of the present disclosure.

In one aspect, the present disclosure includes a method of broadening the pharmacokinetic effects of taurolidine and/or taurultam in a human subject using at least two compounds having different half-lives, comprising administering to the human subject taurolidine and/or taurultam in combination with at least one compound, pharmaceutical composition, or oral dosage form of the present disclosure In one aspect, the present disclosure includes a co-therapeutic composition or regimen including a) at least one compound, pharmaceutical composition, or oral dosage form of the present disclosure, in combination with b) carmustine, cytarabine, gemcitabine, nabPaclitaxel, asparaginase, procarbazine, mitomycin, 5-FU, methotrexate, vinblastine, dacarbazine, cisplatin, carboplatin, paclitaxel, bevacizumab, one or more checkpoint inhibitors, one or more PARP inhibitors, one or more anti-PD-1 drugs, docetaxel, irinotecan (including Onivyde®), doxorubicin, erlotinib, olaparib, lapatinib, topotecan, capecitabine, oxaliplatin, cyclophosphamide, ifosfamide, or a combination thereof.

DETAILED DESCRIPTION OF THE INVENTION

Figure 1:
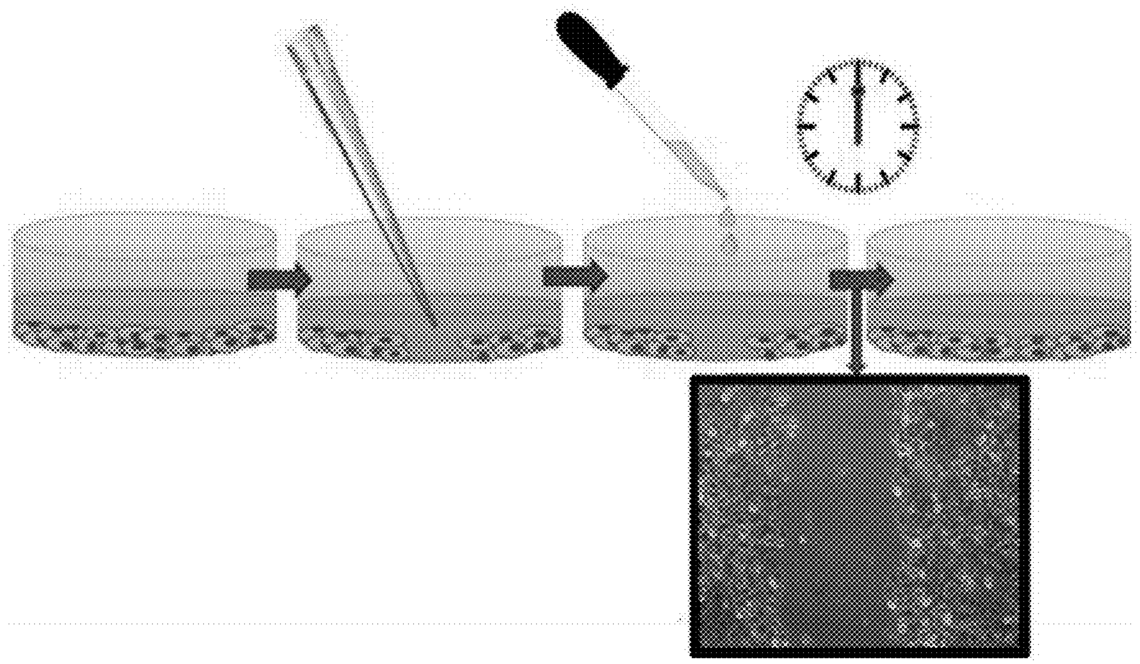
FIG. 1 is a cell migration assay using MDA MB 468 cells.
Figure 1:
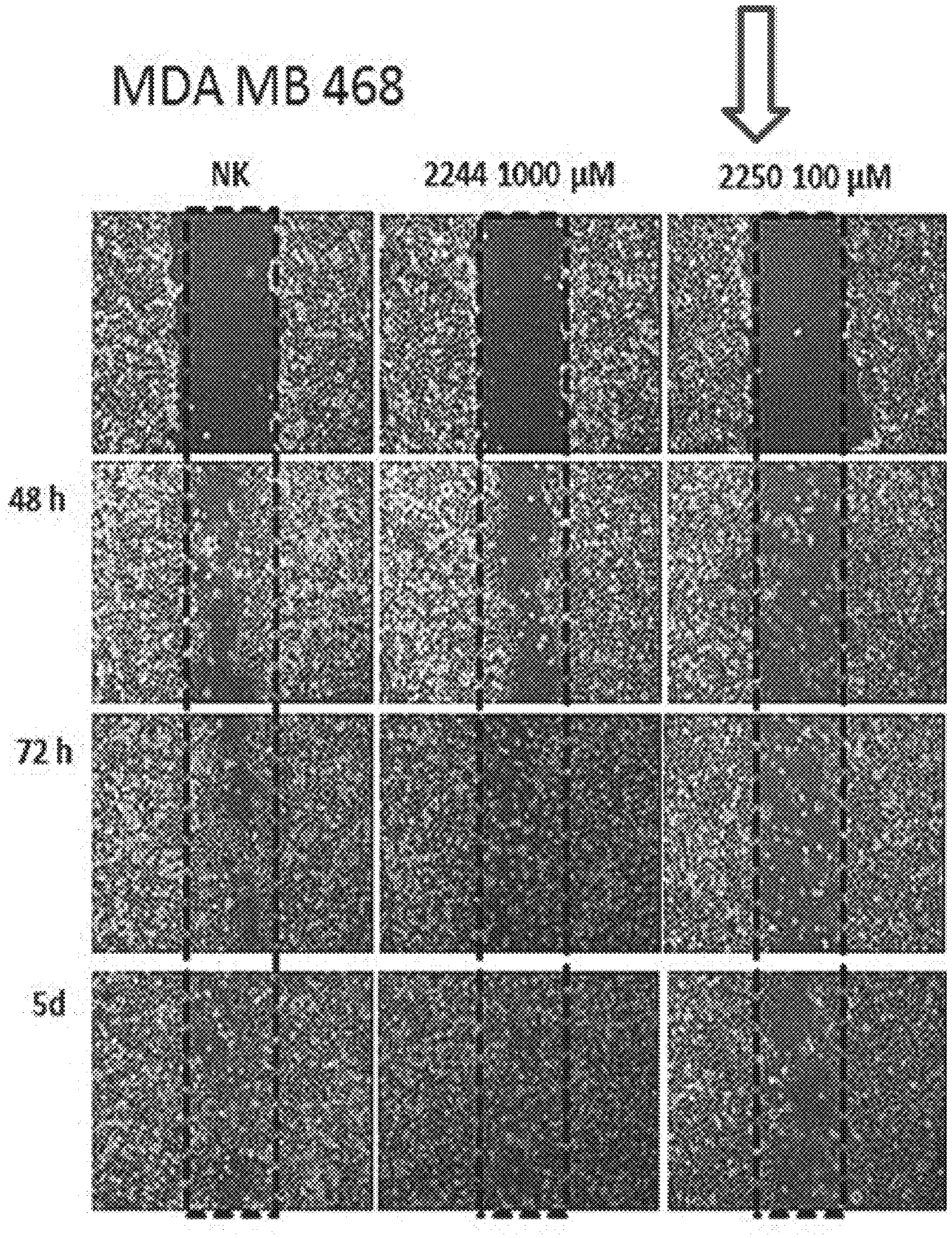
Figure 1:
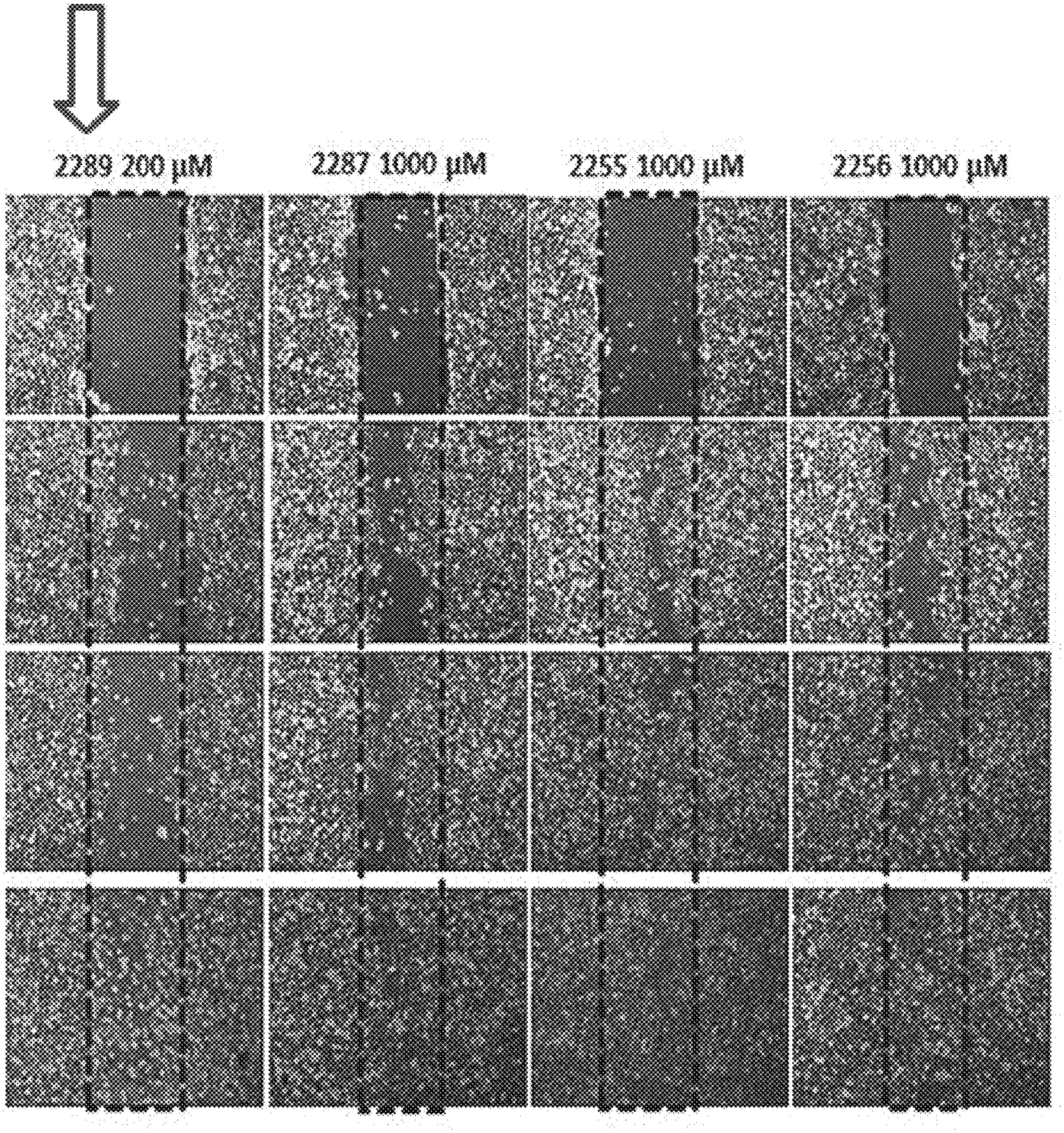

While aspects of the subject matter of the present disclosure may be embodied in a variety of forms, the following description are merely intended to disclose some of these forms as specific examples of the subject matter encompassed by the present disclosure. Accordingly, the subject matter of this disclosure is not intended to be limited to the forms or aspects so described and illustrated.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific aspects of the invention, but their usage does not delimit the invention, except as outlined in the claims.

The terms "inhibiting," "reducing," or "prevention," or any variation of these terms, when used in the claims and/or the specification includes any measurable decrease or complete inhibition to achieve a desired result.

Compounds of the present disclosure may be administered to any subject in need of therapy according to the present disclosure. Such subjects may be at risk of suffering from or suffering from a variety of diseases, disorders and conditions. For example, such diseases, disorders and conditions may be characterized by infection with a microbial agent. In some aspects, diseases, disorders and conditions may be characterized by presence or risk of cancers, tumors, cancer stem cells, a family history of cancer, or positive genetic markers associated with cancer risk.

According to certain embodiments, the present invention relates to compounds having antineoplastic activities, antimicrobial activities and/or other activities.

In certain embodiments, compounds of the present invention are useful, inter alia, in the treatment of cancers and tumors in a subject, such as a human patient. Accordingly, in certain embodiments the present invention also relates to treatment of cancers and tumors using compounds described herein. Cancers such as central nervous system cancers including glioblastoma, glioma, neuroblastoma, astrocytoma, and carcinomatous meningitis, colon cancer, rectal cancer and colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, leukemia, lymphoma, lymphosarcoma, adenocarcinoma, fibrosarcoma, and metastases thereof, for example, are diseases contemplated for treatment according to certain embodiments of the invention. In some aspects, the patient suffers from cancers or tumors including, but not limited to biliary tract cancer; brain cancer, including glioblastomas and medulloblastomas; breast cancer; triple negative breast cancer; uterine cancer; tubal cancer; cervical cancer; choriocarcinoma; colon cancer; bladder cancer; endometrial cancer; retinoblastoma; vaginal cancer; vulvar cancer; esophageal cancer; mouth cancer; gastric cancer; kidney cancer; hematological neoplasms, including acute lymphocytic and myelogenous leukemia; multiple myeloma; AIDS-associated leukemias and adult T-cell leukemia lymphoma; intraepithelial neoplasms, including Bowen's disease and Paget's disease; liver cancer (hepatocarcinoma); lung cancer; head or neck cancers or oral cancers (mouth, throat, esophageal, nasopharyngeal, jaw, tonsil, nasal, lip, salivary gland, tongue, etc.); lymphomas, including Hodgkin's disease and lymphocytic lymphomas; neuroblastomas; neuroendocrine tumors; oral cancer, including squamous cell carcinoma; adrenal cancer; anal cancer; angiosarcoma; appendix cancer; bile duct cancer; bone cancer; carcinoid tumors; soft tissue sarcoma; rhabdomyosarcoma; eye cancer; ovarian cancer, including those arising from epithelial cells, stromal cells, germ cells and mesenchymal cells, and fallopian tube cancer; gallbladder cancer; pancreatic cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; penile cancer; hemangioendothelioma; gastrointestinal cancer; ureteral cancer; urethral cancer; spinal cancer; pituitary gland cancer; primary central nervous system (CNS) lymphoma; thyroid cancer, including thyroid adenocarcinoma and medullar carcinoma; and renal cancer including adenocarcinoma and Wilms tumor. In some aspects, cancers or tumors include breast cancer, prostate cancer, colorectal cancer, lymphoma, multiple myeloma, and melanoma. Drug resistant tumors, for example a multiple drug resistant (MDR) tumor, also are useful in certain embodiments using the inventive compounds, including drug resistant tumors which are solid tumors, non-solid tumors and lymphomas. It is presently believed that any neoplastic cell can be treated using the methods described herein.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the examples described herein.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

Generally herein, the term "or" includes "and" and "and/or."

As used herein, a plurality of compounds or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As will be apparent based on their chemical structures, the compounds of the invention may be useful in one or more of a free acid form, a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. The disclosed compounds, in each of its forms, are within the scope of the invention.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate. Other pharmaceutically acceptable salts include, but are not limited to, hydrochloride, hydrobromide, sulphate, phosphate, tartrate, fumarate, maleate, oxalate, acetate, propionate, succinate, mandelate, mesylate, besylate and tosylate.

Salts, hydrates, esters, or solvates may also be formed with organic bases. Pharmaceutically acceptable base addition salts of acidic compounds may be formed with organic and inorganic bases by conventional methods. For example, alkali metal and alkaline earth metal hydroxides, carbonates and bicarbonates such as sodium hydroxide, potassium hydroxide, calcium hydroxide, potassium carbonate, sodium bicarbonate, magnesium carbonate and the like, ammonia, primary, secondary and tertiary amines and the like. Also aluminum salts of the instant compounds may be obtained by treating the corresponding sodium salt with an appropriate aluminum complex such as, for example, aluminum chloride hexahydrate, and the like. Non-toxic organic bases include, but are not limited to, triethylamine, butylamine, piperazine, and tri(hydroxymethyl)-methylamine. Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxy-methyl)aminoethane; and the like. See, for example, "Pharmaceutical Salts," J. Pharm. Sci., 66:1, 1-19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The salts, hydrates, esters, or solvates of the basic compounds may be prepared either by dissolving the free base of a oxathiazin-like compound in an aqueous or an, aqueous alcohol solution or other suitable solvent containing the appropriate acid or base, and isolating the salt by evaporating the solution. Alternatively, the free base of the oxathiazin-like compound may be reacted with an acid, as well as reacting the oxathiazin-like compound having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172-178, 949-982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since must drugs undergo metabolic transformation of some kind, the biochemical reactions that play a role in drug metabolism may be numerous and diverse. The main site of drug metabolism is the liver, although other tissues may also participate.

Furthermore, certain compositions, concentrations, dosage regimens, dosage amounts, syndromes or conditions, steps, or the like may be discussed in the context of one specific aspect. It is understood that this is merely for convenience, and such disclosure is equally applicable to other aspects found herein. For example, a list of method steps, active agents, kits or compositions described with respect to a method of administering a compound of the present disclosure would find direct support for aspects related to method steps, active agents, kits or compositions of, e.g., the following: treating, preventing, inhibiting or reducing at least one sign or symptom of a disease, disorder or condition caused by or associated with an infection or by presence or risk of cancers, tumors, cancer stem cells, a family history of cancer, or positive genetic markers associated with cancer risk, even if those method steps, active agents, kits or compositions are not re-listed in the context of that aspect in the specification.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease. As used herein, the term "treating" may refer to any administration of a compound of the present invention and includes: (i) preventing or inhibiting the disease in a mammal, e.g., a human, that is experiencing or displaying the pathology or symptomatology of the diseased (i.e., arresting further development of the pathology and/or symptomatology); or (ii) ameliorating the disease in a mammal, e.g., a human that is experiencing or displaying the pathology or symptomatology of the disease (i.e., reversing the pathology and/or symptomatology). The term "controlling" includes preventing, treating, eradicating, ameliorating or otherwise reducing the severity of the condition being controlled.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

Tumor stem cells (also referred to as cancer stem cells (CSCs)) are considered to be the main drivers for the formation of metastases and the regrowth of tumors after resection.

In certain embodiments, compounds of the present invention are useful, inter alia, in the treatment of tumor stem cells in a subject.

In certain embodiments, compounds of the present invention are useful, inter alia, in the treatment of glioblastoma tumor stem cells in a subject.

In certain embodiments, compounds of the present invention are useful, inter alia, in providing an anti-angiogenesis effect in a subject.

In certain embodiments, compounds of the present invention are useful, inter alia, in providing an anti-tubulogenesis effect in a subject.

In certain embodiments, the invention kills tumor cells and/or CSCs, or inhibits their growth, by oxidative stress, apoptosis and/or inhibiting growth of new blood vessels at the tumor site. A primary mechanism of action for killing tumor cells and/or CSCs is oxidative stress. Tumor cells and/or CSCs may also be killed by apoptosis according to the invention. At lower blood concentrations, compounds according to the invention are effective at inhibiting tumor cell growth by their anti-angiogenic action and their anti-tubulogenic action, and these compounds are thus useful for palliative treatment.

The inventive compounds metabolize much slower in the bloodstream than taurolidine and taurultam. Accordingly, lower doses of such compounds can be administered to a patient to achieve similar effects.

Compounds of the present invention also are useful, in certain embodiments, in treatment of microbial infections in a subject, such as a human patient. Microbial infections which may be treated according certain embodiments include bacterial infections, fungal infections and/or viral infections.

Cancer patients tend to be immunocompromised, making them particularly susceptible to microbial infections, especially during and/or after surgery.

In certain embodiments, compounds of the invention are utilized to treat glioblastoma in a subject.

In certain embodiments, compounds of the invention are utilized to treat *S. aureus* infection in a subject.

In certain embodiments, compounds of the invention are utilized according to the invention to treat Methicillin-resistant *Staphylococcus aureus* (MRSA) infection in a subject.

In certain embodiments, compounds of the invention are utilized according to the invention to treat *E. coli* infection in a subject.

In certain embodiments, compounds of the invention are utilized according to the invention to treat *H. pylori* infection in a subject, and/or cancer(s) associated with *H. pylori* in a subject.

In certain embodiments, compounds of the invention are utilized according to the invention to treat *Staphylococcus epidermidis* infection in a subject.

In certain embodiments, compounds of the invention are utilized according to the invention to treat *Streptococcus pneumoniae* infection in a subject.

In certain embodiments, compounds of the invention are utilized according to the invention to treat *Streptococcus pyogenes* infection in a subject.

In certain embodiments, compounds of the invention are utilized according to the invention to treat *Enterococcus faecalis* infection in a subject.

In certain embodiments, compounds of the invention are utilized according to the invention to treat *Haemophilus* influenza infection in a subject.

In certain embodiments, compounds of the invention are utilized according to the invention to treat *Moraxella catarrhalis* infection in a subject.

In certain aspects, compounds of the invention are utilized according to the invention to treat a subject suffering from infection with at least one of the following bacteria: *Enterococcus faecilis, Enterococcus faecilum, Staphylococcus aureus, Clostridium difficile, Acineobacter baumannii, Pseudomonas aeruginosa, Stenotrophomonas maltophilia, Citrobacter freundii, Escherichia coli, Klebsiella pneomoniae, Morganelle morganii, Bactroides fragilis*, and *Helicobacter pylori.*

In certain embodiments, compounds of the invention are utilized according to the invention to treat viral infections in a subject. Viral infections to be treated include human immunodeficiency virus (HV), Herpes simplex viruses, Epstein-Barr virus, SV-40 virus, cytomegalovirus, adenovirus-5, West Nile virus (WNV), dengue virus (DENV), tick-borne encephalitis virus (TBEV), yellow fever virus (YFV), Japanese encephalitis (JEV), influenza, pox virus, smallpox virus, ebola virus, marburg virus, parainfluenza virus, respiratory syncytial virus, rubeola virus, human papillomavirus, varicella-zoster virus, cytomegalovirus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Etheroviruses, Rift Valley fever virus, hepatitis A virus, hepatitis B virus, hepatitis C virus, hepatitis D virus, or hepatitis E virus, zika virus, aroa virus, tyuleniy virus, hanta virus, enteroviruses, echoviruses, calciviruses, sindbis virus, Ross River virus, coronavirus, SARS-coronavirus, Rhabdovirus Family, Vesiculovirus, Lyssavirus, Paramyxovirus Family, Paramyxovirus, Mumps virus, New Castle disease, Morbillivirus, Pneumovirus, Respiratory syncytial virus, Orthomyxovirus, Bunyavirus, Hantavirus, Arenavirus Family, Lassa fever virus, Orbivirus, Colorado Tick fever.

In certain embodiments, compounds of the invention are utilized according to the invention to treat fungal infections in a subject. The compounds of the present disclosure are useful in the curative or prophylactic treatment of fungal infections in animals, including humans. For example, they are useful in treating topical fungal infections in man caused by, among other organisms, species of *Candida, Trichophyton, Microsporum* or *Epidermophyton*, or in mucosal infections caused by *Candida albicans*. They can also be used in the treatment of systemic fungal infections caused by, for example, *Candida albicans, Cryptococcus neoformans, Aspergillus flavus, Aspergillus fumigatus, Coccidiodes, Torulopsis glabrata, Paracoccidioides, Histoplasma* or *Blastomomyces.*

For human use, the antifungal compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. In some aspects, an orally disintegrating tablet may be used. They can be injected parenterally, for example, intravenously, intramuscularly, intravesicularly, or subcutaneously. For parenteral administration, they are best used in the form of a sterile aqueous solution which may contain other substances, for example, enough salts or glucose to make the solution isotonic with blood.

In certain embodiments, compounds according to formula I are utilized according to the invention.

Formula I

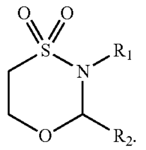

$R_1$ may be —CO-aryl, or C1-C6 branched or unbranched alkyl, e.g., $CH_3$, COH, $COCH_3$, $COCH_2CH_3$, $COCH_2CH_2CH_3$. $R_2$ may be H.

In certain aspects, $R_1$ is not H. In certain aspects, $R_1$ is not benzyl. In certain aspects, $R_1$ is not aryl.

In certain aspects, $R_2$ is not alkyl.

In certain embodiments, new compound 2289 is utilized according to the invention. Compound 2289 has the following structure:

2289

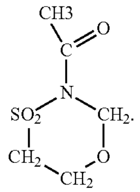

Compound 2289 may be used in treating and inhibiting tumors and cancer stem cells, viral, bacteria, and/or fungal infections.

In certain embodiments, new compound 2293 is utilized according to the invention. Compound 2293 has the following structure:

2293

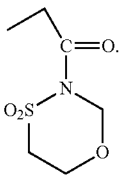

Compound 2293 may be used in treating and inhibiting tumors and cancer stem cells, viral, bacteria, and/or fungal infections.

In certain embodiments, new compound 2296 is utilized according to the invention. Compound 2296 has the following structure:

2296

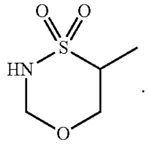

Compound 2296 may be used in treating and inhibiting tumors and cancer stem cells, viral, bacteria, and/or fungal infections.

The amount of the compounds needed depends on tumor size. In one embodiment, the invention includes surgically reducing tumor size and treating with one or more of the compounds. The compound may be administered before, during or after surgery to reduce tumors. Compounds according to the invention can be administered by any suitable method, including without limitation, by capsules, tablets, intravenously (IV), intraperitoneally (IP), intravesicularly, and/or directly to the tumor.

It was unexpectedly found that the compounds could be administered during surgery and immediately after surgery because the compounds do not inhibit wound healing like other chemotherapy agents.

It was unexpectedly found that compounds of the present disclosure kill tumor stem cells, which is very unusual and perhaps unknown among conventional chemotherapy agents. Conventional chemotherapy agents, if effective against tumor stem cells, generally are only effective at very high doses which are extremely toxic to human patients.

It was unexpectedly found that lower doses of taurolidine and/or taurultam killed tumor stem cells than were needed to kill tumor cells.

It was unexpectedly found that compounds of Formula I have a half-life in human blood that is significantly longer than the half-life of taurolidine and taurultam. Accordingly, these compounds are cleared less rapidly from the bloodstream of the patients, thereby effectively delaying loss of drug potency caused by the body's clearance mechanisms.

Thus, the half-life of each of compounds 2289, 2293, and 2296 is about 5 to 6 hours in human blood.

In some embodiments, one or more compounds of the present disclosure, e.g., Formula I, 2289, 2293, and 2296, are administered in compositions at a concentration of about 0.01 to about 1000 μg/ml. In some embodiments, the compounds are administered in compositions at a concentration of about 1 to about 100 μg/ml. In some embodiments, the compounds are administered in compositions at a concentration of about 10 to about 50 μg/ml. The composition may also contain about 0.01 to about 1000 μg/ml, about 1 to about 100 μg/ml, or about 10 to about 50 μg/ml taurolidine and/or taurultam.

In some embodiments, one or more compounds of the present disclosure are administered in compositions at a concentration of about 0.001 to about 5 wt. %, about 0.01 to about 3.5 wt. %, about 0.1 to about 3 wt. %, about 0.5 to about 2.5 wt. %, or about 1 to about 2 wt. %. In some aspects, the oxathiazin-like compound is provided in a composition at a concentration of about 0.01 to about 1.5%. In some aspects, the compound is provided in a composition at a concentration of about 0.1% to about 1%. In some aspects, the compound is provided in a composition at a concentration of about 100 to about 5000 μM, about 250 to about 2500 μM, about 500 to about 2000 μM, about 750 to about 1500 μM, about 1000 to about 1250 μM, or any other concentration within the recited ranges. The composition may additionally contain about 0.01 to about 3%, about 0.1 to about 2.5%, or about 1 to about 2% taurolidine and/or taurultam.

In some aspects, one or more compounds of the present disclosure are provided in a composition in a unit dosage form. As used herein, a "unit dosage form" is a composition containing an amount of compound that is suitable for administration to an animal, such as a mammal, e.g., a human subject, in a single dose, according to a good medical practice. These compositions may contain from about 0.1 mg (milligrams) to about 500 mg, for example from about 5 mg to about 350 mg of compound. The frequency of treatment with the composition of the invention may be changed to achieve and maintain the desired target plasma level. Thus, non-limiting examples of treatment schedules include daily, twice daily, three times daily, weekly, biweekly, monthly, and combinations thereof. Alternatively, the composition of the invention may also be administered as a continuous infusion or a bolus following by one, two, three or more different continuous infusions, e.g., at different rates and dosages of administered drug, such regimens optionally interrupted by one or more additional bolus injections.

In one aspect, the one or more compounds of the present disclosure are provided in a composition that is administered to a subject in need thereof at a total daily dosage may be about 0.001 g to about 1000 g, e.g., about 0.01 g to about 500 g, 0.1 to 300 g, 0.5 to 200 g, 1 g to 100 g, or any amount within the recited range. The daily dosage may be administered in the form of an orally administrable composition. The daily dosage may be administered in the form of a capsule, a tablet, or a pharmaceutically acceptable solution. The daily dosage may be administered in a form that contains one or more compounds of the present disclosure at a concentration of about 0.01 to about 5% w/v, about 0.1 to about 3% w/v, about 0.5 to about 2.5% w/v, or about 1 to about 2% w/v.

The daily dosage may be administered in a form that contains one or more compounds of the present disclosure at a concentration of about 0.001 μg/ml to about 1000 μg/ml, about 0.01 μg/ml to about 750 μg/ml, about 0.05 μg/ml to about 500 μg/ml, about 0.1 μg/ml to about 300 μg/ml, about 0.5 μg/ml to about 200 μg/ml, about 1 μg/ml to about 100 μg/ml, about 5 μg/ml to about 50 μg/ml, about 10 μg/ml to about 25 μg/ml, or about 15 μg/ml to about 20 μg/ml. The daily dosage may be administered in a form that contains one or more solubilizing agents, e.g., polyols.

Effective dosage amounts provided in a composition may include dosage units containing about 0.01-500 mg/kg, about 1-100 mg/kg per day, or about 5-50 mg/kg per day of the e or more compounds of the present disclosure. In some aspects, dosage units are administered every other day, biweekly, or weekly.

In one embodiment, the compounds of Formula I may be administered as a co-therapy with taurolidine and/or taurultam to kill tumor stem cells. In accordance with such an embodiment, the co-therapy has been unexpectedly found to require a lower dosage of drug to kill tumor stem cells than necessary to kill normal tumor cells.

In one embodiment, the compound of Formula I is administered to the subject at a total daily dose of from about 0.1 g to about 100 g, about 1 g to about 80 g, about 2 g to about 50 g, or about 5 g to about 30 g.

Effective dosage amounts of the compounds are dosage units within the range of about 0.1-1,000 mg/kg, preferably 150-450 mg/kg per day, and most preferably 300-450 mg/kg per day.

Suitable formulations for injection or infusion may comprise an isotonic solution containing one or more solubilizing agents, e.g., sugars, polyols, surfactants, osmoticants, in order to provide solutions of increased compound concentration. Such solutions are described in EP 253662B1. The solution can be rendered isotonic with ringer solution or ringer lactate solution. The concentration of the compound in such solutions may be in the range 1-60 g/liter.

The term "polyol" as used herein refers to sugars that contains many hydroxyl (—OH) groups compared to a normal saccharide. Polyols include alcohols and carbohydrates such as mannitol, sorbitol, maltitol, xylitol, isomalt, erythritol, lactitol, sucrose, glucose, galactose, fructose, fucose, ribose, lactose, maltose and cellubiose.

In certain embodiments, the invention also relates to derivatives of the above compounds having, e.g., at least one activity as described herein of said compounds, for example, at least 25%, 30%, 40%, 50%, 60%, 70%, 80%, 90%, 95%, 100%, or more, of said activity.

In certain embodiments, the invention also relates to compositions containing the compounds described herein, including pharmaceutically acceptable solutions of said compounds, as well as orally administrable compositions such as capsules and tablets containing said compositions.

In certain embodiments, the compounds of the present invention can be administered to a subject or patient by any suitable means, for example, in solution, e.g., locally, systemically such as by intravenous infusion, or the like.

Synthesis of 2289

Compound 2289 was prepared according the following non-limiting synthesis protocols:

1. The following compound:

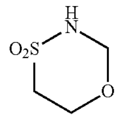

was reacted with acetic anhydride in the presence of pyridine and at a temperature of about 100° C. to form compound 2289. Compound 2289 was isolated from the reaction mixture by adding water and filtering the precipitation. Yield (raw): 89%.

2. The following compound:

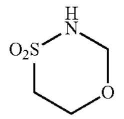

was reacted with acetyl chloride in the presence of pyridine and at a temperature of about 60° C. to form compound 2289. Compound 2289 was isolated from the reaction mixture by adding water and filtering the precipitation. Yield (crude): 57%.

Purification:

Re-crystallization with, e.g.,

Ethanol

Ethyl acetate

Ethyl acetate/light petroleum

Physical Properties

Melting range: 79-83° C.

Solubility in water: about 1.5% at room temperature

Identity was verified by NMR, IR and elemental analysis.

In some aspects, the present disclosure includes a method of making compound 2289 by the following reaction:

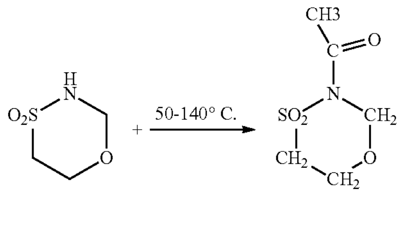

-continued

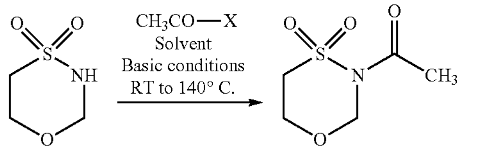

GP-2250

2289

In some aspects, X is a leaving group. For example, X may be an acyl halide wherein the halogen is, e.g., Cl, Br, I. In another example, X may be an anhydride such as CO═OR. As another example, X may be a thioester SR or an ester OR. As another example, X may be mesylate or tosylate. As another example, X may be a halogen.

Synthesis of 2293

Compound 2293 was prepared according the following non-limiting synthesis protocol:

The following compound:

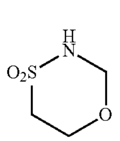

was reacted with propionyl chloride in the presence of pyridine to form compound 2293. Compound 2293 stays in the pyridine phase and can be isolated, e.g., by column chromatography.

Purification:

Column Chromatography: Eluent hexane/ethyl acetate 50:50

Physical Properties

Melting range: 52-53° C.

Solubility in water: <1.5% at room temperature

Identity was verified by NMR, IR and MS.

In some aspects, the present disclosure includes a method of making compound 2293 by the following reaction:

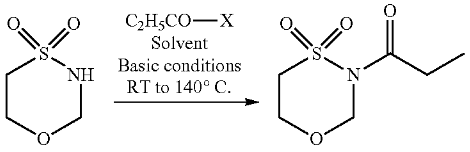

GP-2250

2293

In some aspects, X is a leaving group. For example, X may be an acyl halide wherein the halogen is, e.g., Cl, Br, I. In another example, X may be an anhydride such as CO═OR. As another example, X may be a thioester SR or an ester OR. As another example, X may be mesylate or tosylate. As another example, X may be a halogen.

Synthesis of 2296

Compound 2296 was prepared according the following non-limiting synthesis protocol:

1-hydroxypropane-2-sulfonamide was dissolved in water and reacted with methylene glycol to form compound 2296.

Yield (crude): 51%

Purification:

Re-crystallization with alcoholic solvents.

Physical Properties

Melting range: 74-75° C.

Solubility in water: min. 1% at room temperature

Identity was verified by NMR, IR and elemental analysis.

In some aspects, the present disclosure includes a method of making compound 2296 by the following reaction:

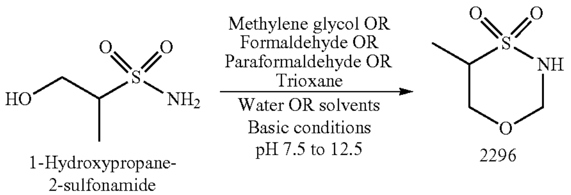

1-Hydroxypropane-2-sulfonamide

2296

The reactants depicted above are alternatives and non-limiting. Those skilled in the art will recognize that other alternative reactants may be used in the reaction. A wide range of solvents may be used including but not limited to alcohols, e.g., ethanol or methanol, acetonitrile, tetrahydrofuran (THF), ethyl acetate, and the like.

In certain embodiments, a sublimation apparatus, comprised of laboratory glassware known in the art, may be used in a technique of sublimation to purify compounds according to the invention. In certain embodiments, a sublimation vessel is heated under vacuum and under reduced pressure. The compound volatizes and condenses as a purified compound on a cooled surface, leaving non-volatile residue impurities behind. This cooled surface often takes the form of a cold finger. After heating ceases and the vacuum is released, the sublimed compound can be collected from the cooled surface.

In one embodiment, this disclosure includes a method of killing tumor stem cells by administering to a subject in need thereof a tumor stem cell killing effective amount of taurolidine, taurultam, or a mixture thereof in combination with one or more compounds of Formula I. The tumor stem cell killing effective amount of taurolidine and/or taurultam is less than an amount of taurolidine and/or taurultam required for killing tumor cells. In some aspects, the compounds of Formula I are co-administered with carmustine, cytarabine, gemcitabine, nabPaclitaxel, asparaginase, procarbazine, mitomycin, 5-FU, methotrexate, vinblastine, dacarbazine, cisplatin, carboplatin, paclitaxel, bevacizumab, one or more checkpoint inhibitors, one or more PARP inhibitors, one or more anti-PD-1 drugs, docetaxel, irinotecan (including Onivyde®), doxorubicin, erlotinib, olaparib, lapatinib, topotecan, capecitabine, oxaliplatin, cyclophosphamide, ifosfamide, or a combination thereof. In some aspects, the treatment is for ovarian cancer and the compound of Formula I is co-administered with Carboplatin, Paclitaxel, Topotecan, Bevacizumab, one or more PARP inhibitors, one or more anti-PD-1 drugs, or a combination thereof. For example, the one or more PARP inhibitors may include Olaparib (Lynparza®), Niraparib (Zejula®), Rucaparib (Rubraca®), and Talazoparib (Talzenna®), Veliparib, Pamiparib, CEP9722, E7016, Iniparib, 3-Aminobenzamide, or a combination thereof. For example, the one or more anti-PD1 drugs may include Pembrolizumab (Keytruda®), Nivolumab (Opdivo®), Cemiplimab (Libtayo®), Atezolizumab (Tecentriq®) Avelumab (Bavencio®), and Durvalumab (Imfinzi®). For example, the co-administered drug may include Pembrolizumab (Keytruda®), Nivolumab (Opdivo®), Cemiplimab (Libtayo®), Spartalizumab, Camrelizumab, Sintilimab, Tislelizumab, Toripalimab, Dostarlimab, Ratifanlimab, Sasanlimab, Budigalimab, Zimberelimab, BI754091, JTX-4014, AMP-224, AMP-514, Atezolizumab (Tecentriq®), Avelumab (Bavencio®), Durvalumab (Imfinzi®), Cosibelimab, KN035, CK-301, AUNP12, CA-170, BMS-986189, or a combination thereof. In some aspects, the treatment is for pancreatic cancer and the compound of Formula I is co-administered with one or more of the foregoing compounds suitable for treating pancreatic cancer.

The phrases "co-administering" or "administering in combination" as used herein mean that two (or more) agents are administered in temporal juxtaposition. The co-administration or combination may be effected by the two agents being mixed into a single formulation, or by the two agents being administered separately but simultaneously, or separately and within a short time of each other. For example, in general the two agents are co-administered within the time range of 6-168 hours. In this case, the agents may be administered in either order, i.e. the chemotherapeutic drug may be administered first, or the one or more compound of the present disclosure may be administered first. In some aspects, the two agents are co-administered in a single formulation, or are co-administered sequentially and separately.

In some embodiments, the taurolidine, taurultam, or a mixture thereof is administered in a tumor stem cell killing composition at a concentration of about 0.01 to about 500 μg/ml. In some embodiments, the taurolidine, taurultam, or a mixture thereof is administered in a tumor stem cell killing composition at a concentration of about 0.1 to about 100 μg/ml. In some embodiments, the taurolidine, taurultam, or a mixture thereof is administered in a tumor stem cell killing effective composition at a concentration of about 10 to about 50 μg/ml. Taurolidine is effective at killing tumor stem cells in tissue culture in vitro at 0.01 μg/ml.

In some embodiments, the taurolidine, taurultam, or a mixture thereof is administered in a tumor stem cell killing composition at a concentration of about 0.001 to about 2%. In some embodiments, the taurolidine, taurultam, or a mixture thereof is administered in a tumor stem cell killing composition at a concentration of about 0.01 to about 1.5%. In some embodiments, the taurolidine, taurultam, or a mixture thereof is administered in a tumor stem cell killing composition at a concentration of about 0.1% to about 1%.

In one embodiment, the taurolidine, taurultam, or a mixture thereof is administered for tumor stem cell killing to a subject in need thereof at a total daily dose of from about 0.01 g to about 50 g, about 0.1 g to about 30 g, about 0.5 g to about 10 g, or about 1 g to about 5 g.

Tumor stem cell killing effective dosage amounts of the taurolidine, taurultam, or a mixture thereof are dosage units within the range of about 0.01-500 mg/kg, preferably 1-100 mg/kg per day, and most preferably 5-50 mg/kg per day.

In another embodiment, this disclosure includes a method of killing tumor stem cells by administering to a subject in need thereof one or more compounds of the present disclosure alone or in combination with taurolidine and/or taurultam. Such a technique provides a method for killing tumor stem cells using at least two compounds having different half-lives, and thereby broadening the pharmacokinetic effects obtained thereby.

In some aspects, the present disclosure includes broadening the therapeutic window of a taurolidine and/or taurultam therapy by co-administering taurolidine and/or taurultam with or more compounds of the present disclosure.

In certain aspects, the following experimental protocols are performed:

Cell Lines and Culture Conditions

Four different human cancer cell lines are used in testing the compounds of the present disclosure: pancreatic cancer cells Panc TuI (CLS Cell Lines Service, Eppenheim, Germany), Colon cancer cells HCT116 (ATCC-LGC Standards GmbH, Wesel, Germany), merkel cell carcinoma cells MCC 14.2 and Mammary Gland/Breast cancer cells MDA MB 468 (ATCC-LGC Standards GmbH, Wesel, Germany). HCT 116, MDA MB 468 and Panc TuI cells are cultured in Dulbecco's Modified Eagle Medium (DMEM), MCC 14.2 is maintained in RPMI 1640. All cultures are supplemented with penicillin (100 U/ml), streptomycin (100 U/ml) and 2 mM L-Glutamine. MCC 14.2 cells are further complemented with 25 nM HEPES. Cells are grown as monolayer at 37° C. and 5% $CO_2$ in a humidified atmosphere.

Different gram-negative and gram-positive bacteria are used for testing the compounds of the present disclosure: *Staphylococcus aureus* and *Escherichia coli* (ATCC-LGC Standards GmbH, Wesel, Germany); *Enterococcus faecilis, Enterococcus faecilum, Staphylococcus aureus, Clostridium difficile, Acineobacter baumannii, Pseudomonas aeruginosa, Stenotrophomonas maltophilia, Citrobacter freundii, Escherichia coli, Klebsiella pneomoniae, Morganelle morganii, Bactroides fragilis, Helicobacter pylori* (fresh clinical isolates). All isolates are cultured with Müller-Hinton-Agar excluding *Bacteroides fragilis* and *Helcobacter pylori. Bacteroides fragilis* is cultured with Müller-Hinton-Agar containing 5% Horseblood and 20 mg/l ß-NAD. *Helicobacter pylori* is cultured with Chocolat PolyViteX-Agar.

Cell Migration Assay

Cells are plated into the 60-mm dishes to create a confluent monolayer and are incubated for 24 hours allowing cells to adhere and spread. The required number of cells for a confluent monolayer depends on the particular cell type. After creating a scratch of the cell monolayer, the gaparea is examined by phase-contrast-microscopy. Images are captured at the beginning and at regular intervals during cell migration (48, 72, and 120 hours (5 d)) closing the scratch, to semi-quantify the migration rate of the cells.

MTT Cytotoxicity Assay

Cells are seeded individually to obtain a sub confluent monolayer in a 96 well plate format and are incubated for 24 hours prior treatment. To examine a dose response regarding the antineoplastic activity cells are incubated with increasing concentrations (100, 200, 500, 1000, 1500, 2000 μmol/l) of all different Oxathiazinane derivatives and $ddH_2O$ as control for 24 and 48 hours. After the exposition time 10 μl MTT (3-(4,5-Dimethylthiazol-2-yl)-2,5-diphenyltetrazoliumbromid) reagent (5 mg/ml) is added and incubated for 2 hours before violet Formazan crystals are dissolved in 100 μl DMSO (Dimethylsulfoxide). Viability of the cells can be analyzed by using a microplate absorbance reader by measuring the OD560 (ASYS, UVM340, Anthos Mikrosystheme GmbH, Germany). The assay is performed using 8 replicates in three independent experiments with consecutive passages.

ROS Analysis

To get further insights into the functional aspects, the impact of the compounds on the cellular level of reactive oxygen species (ROS) is analyzed using the Cellular ROS/Superoxide Detection Assay KIT (Abcam, Cambridge, UK) following the manufactures instructions.

BrdU Proliferation Assay

Cells are seeded individually to obtain a sub confluent monolayer in a 96 well plate format and are incubated for 24 hours prior to treatment. To examine the dose response regarding their anti-proliferative activity, cells are incubated with increasing concentrations (100, 200, 500, 1000, 1500 and 2000 μmol/l) of all different Oxathiazinane derivates and $ddH_2O$ as control for 6 h prior BrdU proliferation assay (5-bromo-2-deoxyuridine)-ELISA (Roche Applied Science, Mannheim, Germany) according to the manufacturer's instructions. The incubation time of 6 hours has been shown to be appropriate for the BrdU proliferation assay in previous experiments. The amount of synthesized DNA is detected using a microplate absorbance reader measuring at 370 nm with a reference wavelength of 492 nm (ASYS, UVM340, Anthos Mikrosysteme GmbH, Krefeld, Germany). BrdU assays are performed with 8 replicates of three independent experiments with consecutive passages.

Disc Diffusion Test

The antibacterial potential of compounds is examined by the Kirby-Bauer disc diffusion test using Müller-Hington agar. A 10 mm diameter disk soaked in 150 μl of distilled water containing 10 mg of the test substance was placed on Müller-Hington agar (bioMeieux, Geneve, Switzerland) holding a pre-lawn of the according test bacteria. The plates are incubated at 37° C. for 24 hours and the zone of inhibition is recorded. Culture media and sterilized distilled water were used as a control. N-acetylcysteine (NAC) is used as an anti-oxidant control.

Statistics

Results of MTT and BrdU assay (percentage of living/proliferating cells) are expressed as means±SEM. One-way ANOVA is used, followed by Tukey's post-hoc test comparing experimental groups with normal distribution and Fisher's exact test for categorical data, if appropriate. P-values≤0.05 are considered as statistically significant.

EXAMPLES

Example 1

Cell migration assay: cell migration of compounds 2289, 2244, 2287, 2255, 2256 compared to non-treated control (NK) and positive control (compound 2250). Comparative compounds 2244, 2287, 2255, 2256 have the following structures:

2244

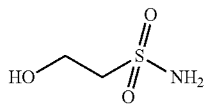

2255

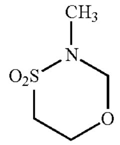

2256

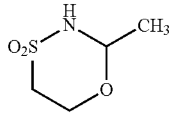

2287

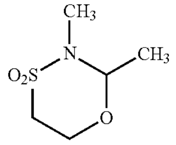

Using cell migration assays, the migration rate of different cancer cell entities under treatment with 2289, negative control and positive control (2250) was semi-quantified. FIG. 1 displays the results after 2 to 5 days illustrated exemplarily using a confluent monolayer of MDA MVB 468.

As shown in FIG. 1, compared to the untreated control where the cells have migrated far into the scratch area to close the gap, the migration rate in cultures treated with 2250 was clearly inhibited. Cell cultures treated with 2289 also showed a lower migration rate although less than with 2250. All other tested derivatives had no reduced migration rate, showing nearly completely closed gaps after 5 days, comparable to the untreated control. The results are representative for all tested cell lines.

Example 2

Anti-neoplastic activity of compounds 2289, 2293, and 2296 was determined according to the MTT assay and BrdU assay described above.

Figure 2:
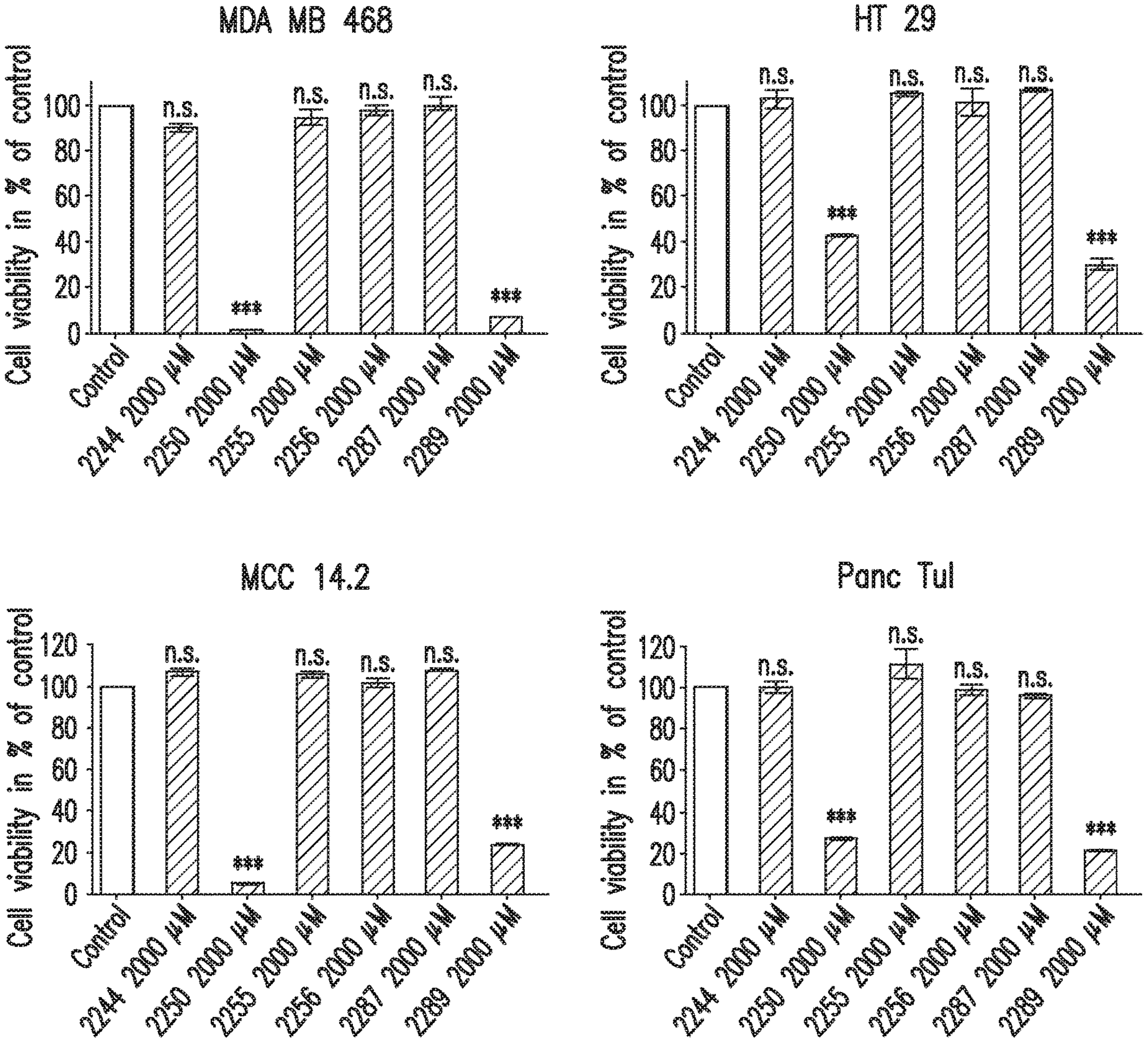
FIG. 2 is a MTT assay for cell viability

As shown in FIG. 2, in the MTT assay for cell viability, 2250 and 2289 showed significant reduction of living cells within all tested cancer cell lines (MDA MB 468, HT29, MCC 14.2, Panc TuI) with varying susceptibility towards both substances (with MDA MB 468 showed the highest; HT 29 the lowest response rates).

Figure 3:
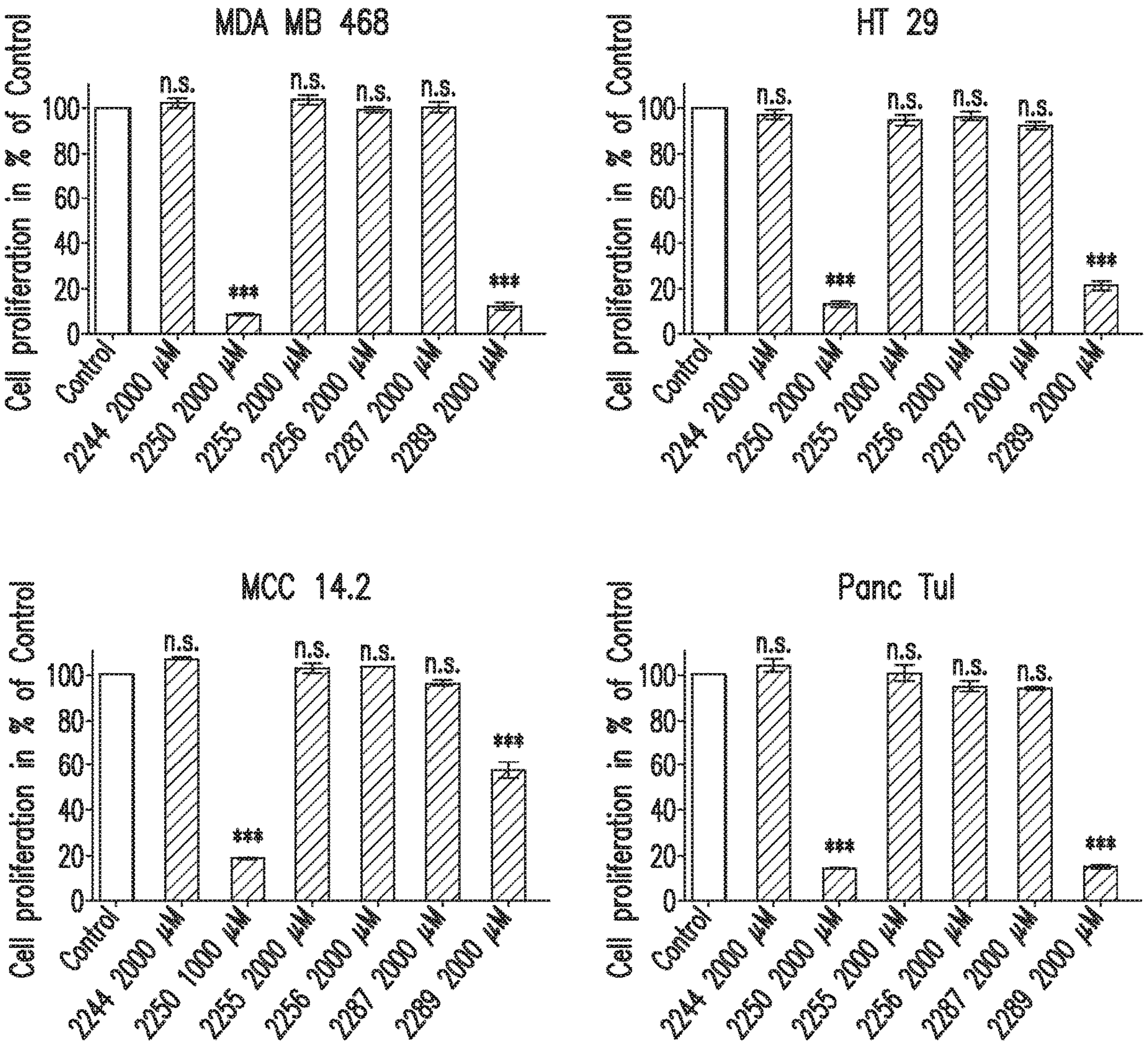
FIG. 3 is a BrdU assay for cell proliferation.

As shown in FIG. 3, in the BrdU assay for cell proliferation, 2250 and 2289 show a significant reduction of proliferating cells within all tested cancer cell lines with MDA MB 468 showed the highest and MCC 14.2 the lowest response rates. 2250 shows all over a higher anti-proliferative capacity compared to 2289.

Example 3

Anti-bacterial activity of compounds 2289, 2250, 2244, 2255, 2256, 2287, 2289, 2293, and 2296 was determined using an agar diffusion test. The results are summarized as follows:

| Compound | Zone of inhibition | Bacterial Strains Tested |
|---|---|---|
| 2250 | ++ (24.5 mm; 49.5 mm; 42.5 mm) | Different a.o. *Escherichia coli*, *Staphylococcus aureus* (MRSA), *Enterococcus faecalis* |
| 2244 | -- (<10 mm) | Different a.o. *Escherichia coli*, *Enterococcus faecium* |
| 2255 | -- (<10 mm) | Different a.o. *Escherichia coli*, *Staphylococcus aureus* (MRS |
| 2256 | -- (<10 mm) | *Escherichia coli*, *Staphylococcus aureus* (MRSA) |
| 2287 | -- (<10 mm) | *Escherichia coli*, *Staphylococcus aureus* (MRSA) |
| 2289 | ++ (18.5 mm; 27.5 mm) | *Escherichia coli*, *Staphylococcus aureus* (MRSA) |

2289: Inhibition Zone of Different Bacterial Strains
- *Escherichia coli* (ATCC 8739), gram-negative: 18.5 mm
- *Staphylococcus aureus* (ATCC 6538), gram-positive: 27.5 mm 2293: Inhibition Zone of Different Bacterial Strains
- *Escherichia coli* (ATCC 8739), gram-negative: 19.5 mm
- *Staphylococcus aureus* (ATCC 6538), gram-positive: 31.5 mm
- *Staphylococcus aureus* (MRSA Nr. 2065), gram-positive: 32.5 mm 2296: Inhibition Zone of Different Bacterial Strains
- *Escherichia coli* (ATCC 8739), gram-negative: 23.0 mm
- *Staphylococcus aureus* (ATCC 6538), gram-positive: 38.0 mm

*Staphylococcus aureus* (MRSA Nr. 2065), gram-positive: 43.0 mm

Example 4

Figure 4:
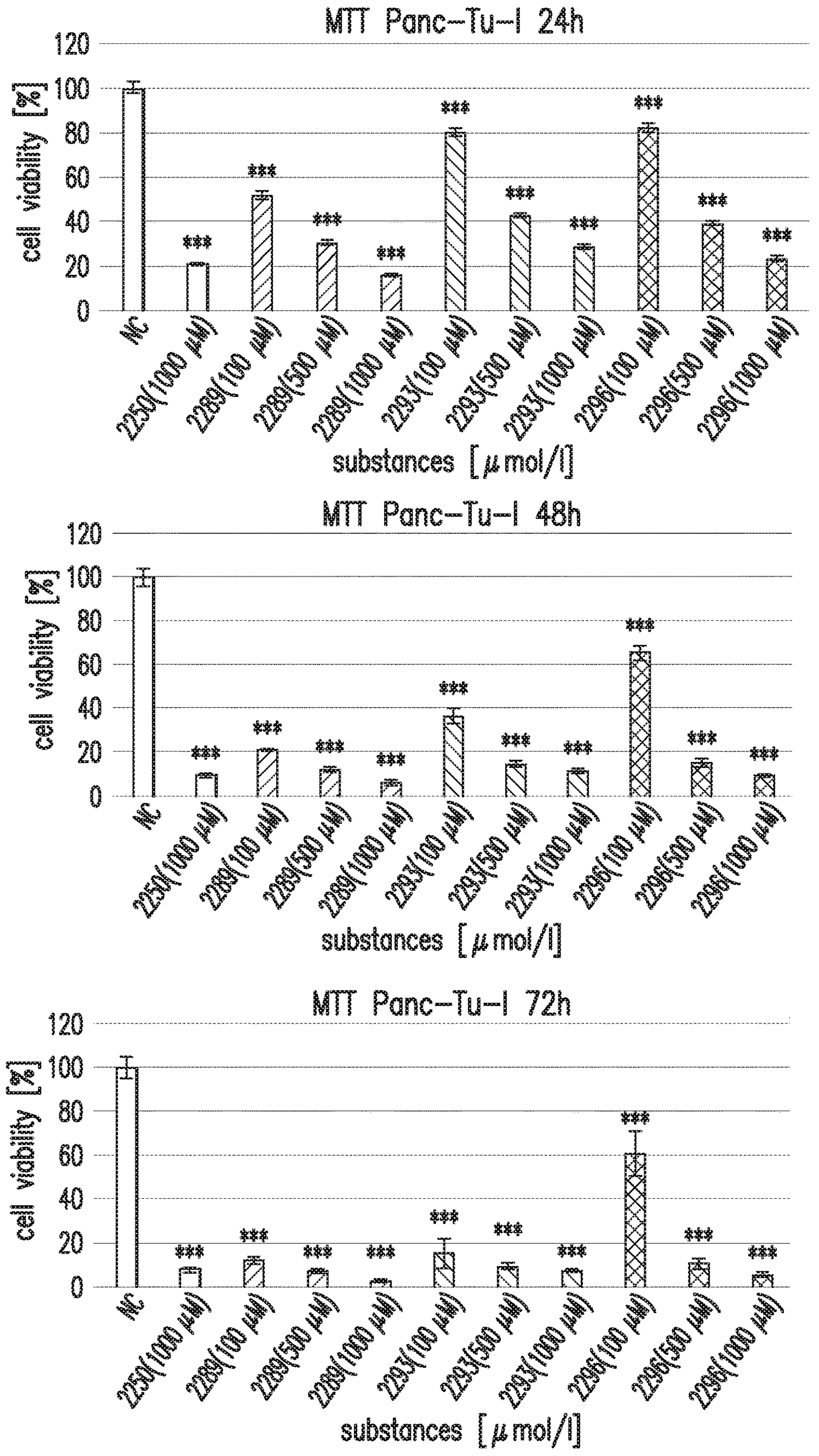
FIG. 4 shows the results of a MTT cytotoxicity assay for Panc TuI cells with different concentrations of compounds 2289, 2293, and 2296 compared to a negative control=NC of untreated cells and a positive control of 1000 μM GP2250 after an incubation period of 24 h, 48 h and 72 h. All substances show a significant impact on the cell viability of the analyzed cell line Panc TuI from a concentration of 100 μM compared to the untreated control (NC) after 24 h. Measurements were performed in eightfold determination and p-values were calculated by a t-test. (* $p \leq 0.05$ significant,  $p \leq 0.01$ highly significant, * $p \leq 0.001$ extremely significant).

A MTT Cytotoxicity assay of the cell line Panc TuI with different oxathiazine derivatives was performed. FIG. 4 shows the cell viability under the influence of different concentrations of the substances 2289, 2293 and 2296 in different concentrations compared to a negative control=NC of untreated cells and a positive control of 1000 μM GP2250 after an incubation period of 24 h, 48 h and 72 h.

All substances show a significant impact on the cell viability of the analyzed cell line Panc TuI from a concentration of 100 μM compared to the untreated control (NC) after 24 h.

Figure 5:
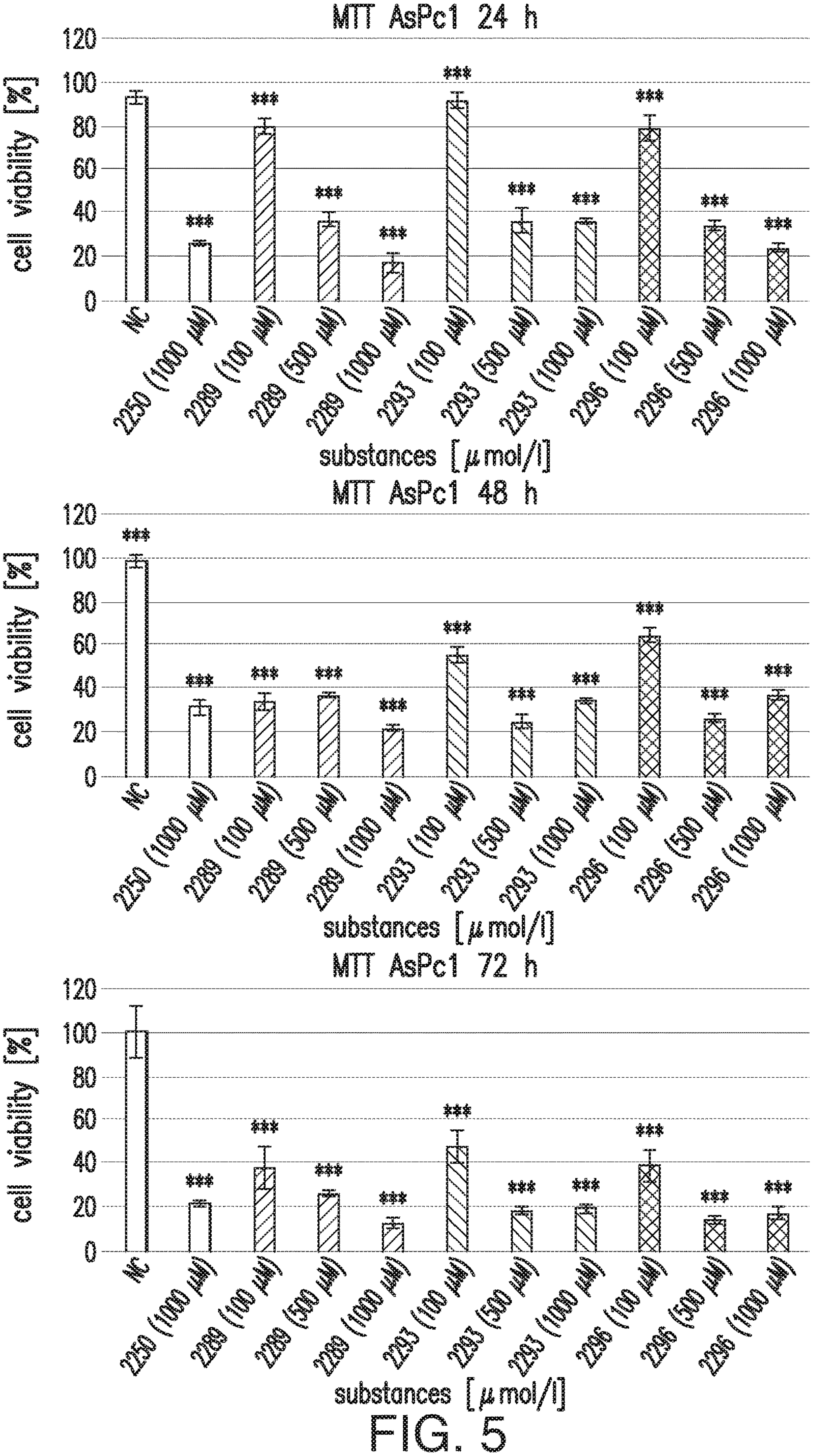
FIG. 5 shows the results of a MTT cytotoxicity assay for AsPc1 cells with different concentrations of compounds 2289, 2293, and 2296 compared to a negative control=NC of untreated cells and a positive control of 1000 μM GP2250 after an incubation period of 24 h, 48 h and 72 h. Substances 2289 and 2296 show a significant impact on the cell viability of the analyzed cell line AsPc1 from a concentration of 100 μM compared to the untreated control (NC) after 24 h. The substance 2293 shows a significant impact on the cell viability from a concentration of 500 μM compared to the untreated control (NC) after 24 h. Measurements were performed in eightfold determination and p-values were calculated by a t-test. (* $p \leq 0.05$ significant,  $p \leq 0.01$ highly significant, * $p \leq 0.001$ extremely significant).

A MTT Cytotoxicity assay of the cell line AsPc1 with different oxathiazine derivatives was performed. FIG. 5 shows the cell viability under the influence of different concentrations of the substances 2289, 2293 and 2296 in different concentrations compared to a negative control=NC of untreated cells and a positive control of 1000 μM GP2250 after an incubation period of 24 h, 48 h and 72 h.

Substances 2289 and 2296 showed a significant impact on the cell viability of the analyzed cell line AsPc1 from a concentration of 100 μM compared to the untreated control (NC) after 24 h. The substance 2293 shows a significant impact on the cell viability from a concentration of 500 μM compared to the untreated control (NC) after 24 h.

Figure 6:
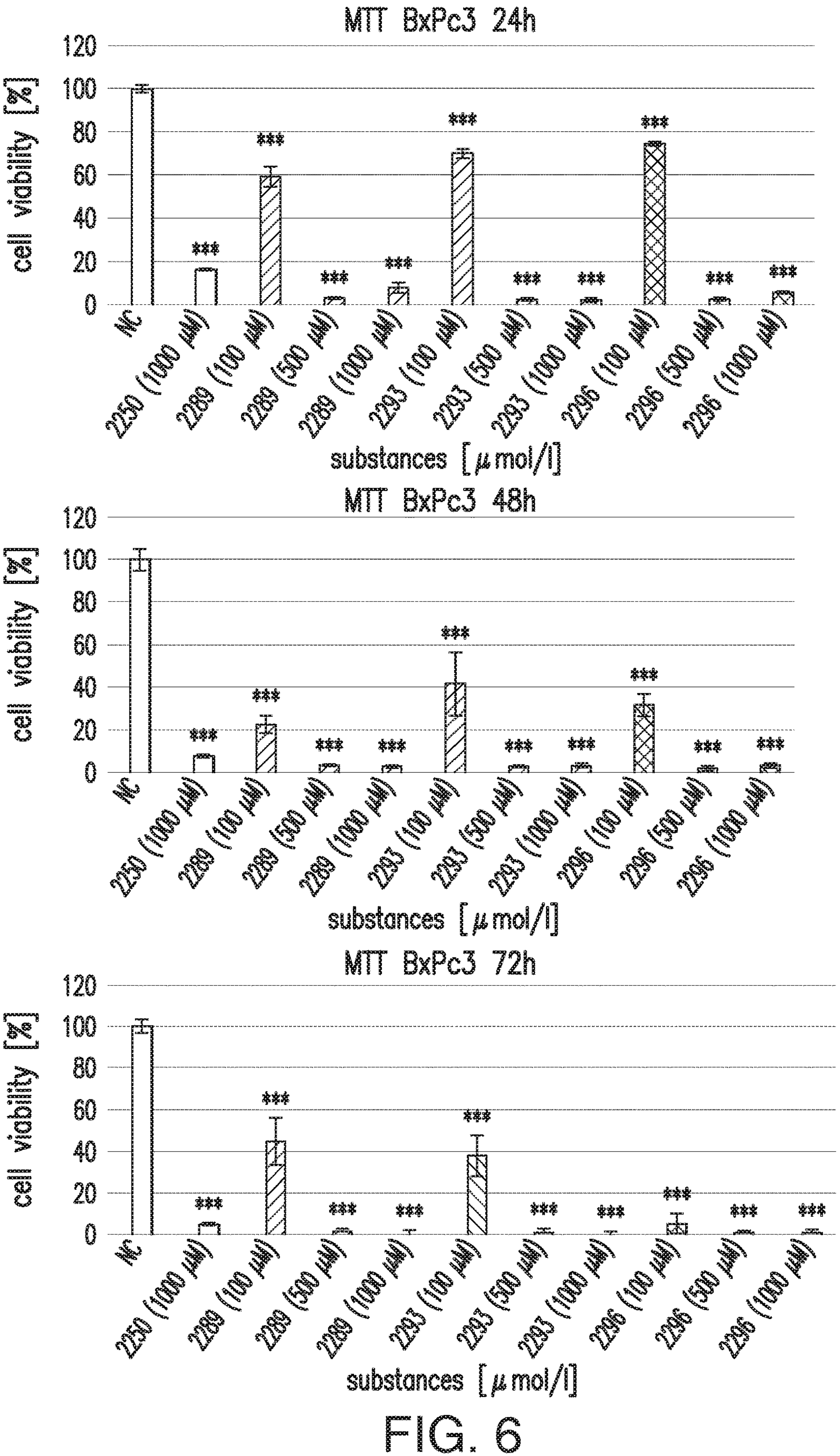
FIG. 6 shows the results of a MTT cytotoxicity assay for BxPc3 cells with different concentrations of compounds 2289, 2293, and 2296 compared to a negative control=NC of untreated cells and a positive control of 1000 μM GP2250 after an incubation period of 24 h, 48 h and 72 h. All substances show a significant impact on the cell viability of the analyzed cell line BxPc3 from a concentration of 100 μM compared to the untreated control (NC) after 24 h. Measurements were performed in eightfold determination and p-values were calculated by a t-test. (* $p \leq 0.05$ significant,  $p \leq 0.01$ highly significant, * $p \leq 0.001$ extremely significant).

A MTT Cytotoxicity assay of the cell line BxPc3 with different oxathiazine derivatives was performed. FIG. 6 shows the cell viability under the influence of different concentrations of the substances 2289, 2293 and 2296 in different concentrations compared to a negative control=NC of untreated cells and a positive control of 1000 μM GP2250 after an incubation period of 24 h, 48 h and 72 h. All substances show a significant impact on the cell viability of the analyzed cell line BxPc3 from a concentration of 100 μM compared to the untreated control (NC) after 24 h.

Figure 7:
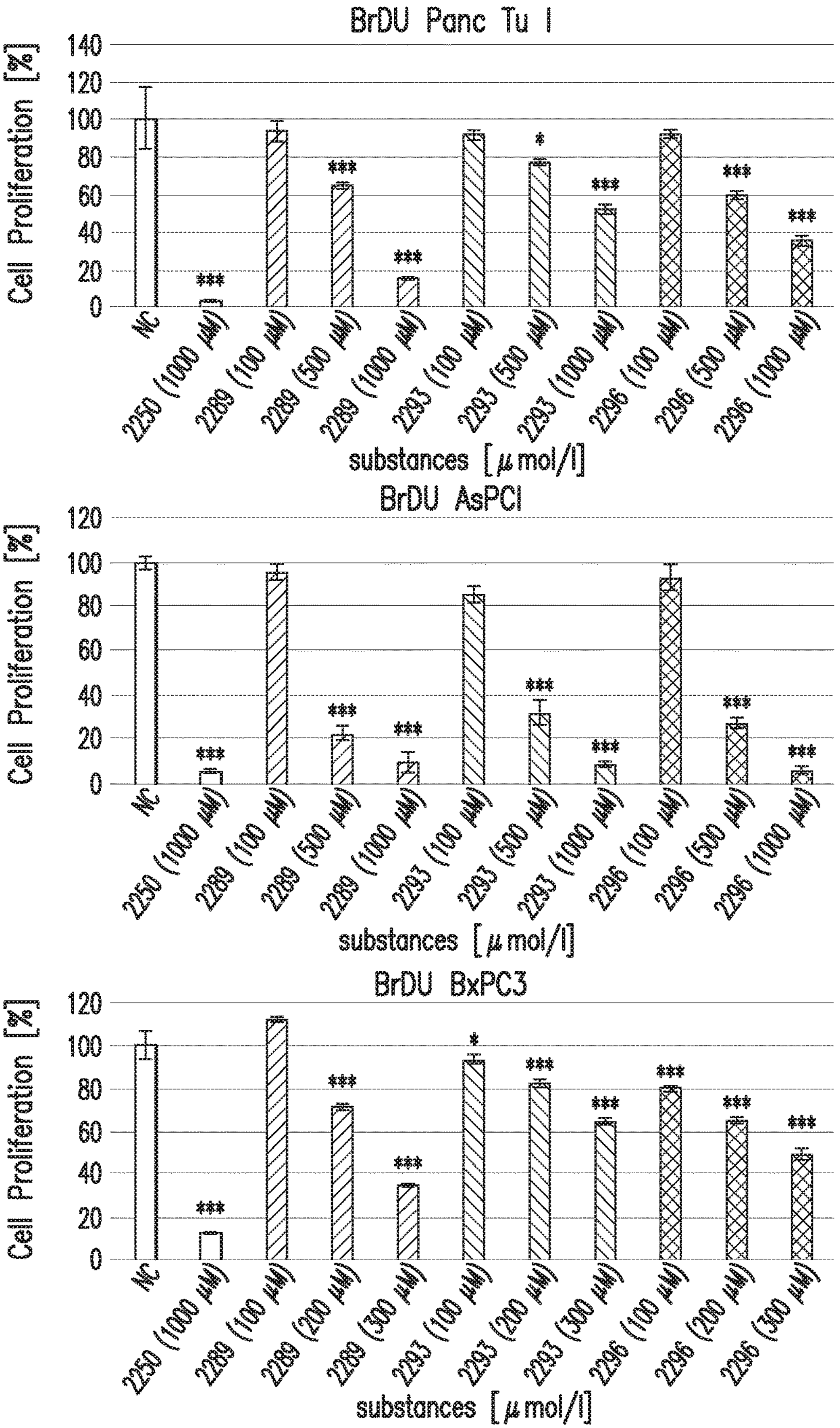
FIG. 7 shows the results of a proliferation assay of the cell lines Panc TuI, AsPc1 and BxPc3 under the influence of different concentrations of the substances 2289, 2293 and 2296 in different concentrations compared to a negative control=NC of untreated cells and a positive control of 1000 μM GP2250 after an incubation period of 6 h. All substances show a significant impact on the cell proliferation of all analyzed cell lines from a concentration of 500 μM compared to the untreated control (NC). Measurements were performed in eightfold determination and p-values were calculated by a t-test. (* $p \leq 0.05$ significant,  $p \leq 0.01$ highly significant, * $p \leq 0.001$ extremely significant).

A proliferation assay of the cell lines Panc TuI, AsPc1 and BxPc3 with different oxathiazine derivatives was performed. FIG. 7 shows the cell proliferation under the influence of different concentrations of the substances 2289, 2293 and 2296 in different concentrations compared to a negative control=NC of untreated cells and a positive control of 1000 μM GP2250 after an incubation period of 6 h. All substances show a significant impact on the cell proliferation of all analyzed cell lines from a concentration of 500 μM compared to the untreated control (NC).

Example 5

It has been previously reported that taurolidine has a half-life of about 30 minutes, whereas compound 2250 has a significantly longer half-life. The half-life of each of compounds 2289, 2293, and 2296 in human fresh blood was measured at 37° C. in vitro.

For 2289 and 2293 into 2250, K2-EDTA human blood was spiked with 2289 or 2293 at 256 μM; 2250 at 26 μM and 2244 at 26 μM (n=1). The pool remained at 37° C. for 20-25 min and then an aliquot was centrifuged (2500 g for at least 5 minutes at 4° C.). After centrifugation the human plasma was collected and immediately frozen at −80° C. This aliquot corresponded to the T0.

The remaining pool was aliquoted and kept at 37° C. An aliquot was collected, centrifuged (2500 g for at least 5 minutes at 4° C.) and the recovered plasma was frozen at −80° C. after at least 0.25, 0.5, 1, 6, 8, 24 and 48 hours.

Stability was determined by measuring the 2289 and 2293 peak area at each time point compared to T0.

For 2296 into its metabolite 1-hydoxypropane-2-sulfonamide, K2-EDTA human blood was spiked with 2296 at 256 μM and 1-hydroxypropane-2-sulfonamide at 26 μM (n=1).

The pool remained at 37° C. for 20-25 min and then an aliquot was centrifuged (2500 g for at least 5 minutes at 4° C.). After centrifugation the human plasma was collected and immediately frozen at −80° C. This aliquot corresponded to the TO.

The remaining pool was aliquoted and kept at 37° C. An aliquot was collected, centrifuged (2500 g for at least 5 minutes at 4° C.) and the recovered plasma frozen at −80° C. after at least 0.5, 1, 3, 6, 8 and 24 hours/

Stability was determined by measuring 2296 peak area at each time point compared to T0.

The results unexpectedly demonstrated that compound 2296 has a very similar profile human blood stability to 2250:

Blood Stability Results for 2296 in Presence of 1-Hydroxy-propane-2-Sulfonamid

| 2 | 2296 into 1-hydroxypropane-2-sulfonamide at 37° C. | | | |
|---|---|---|---|---|
| QC | Time (h) | Area | Mean | % Stability |
| 1 | 0 | 481875.6 | 478360.75 | 100 |
| 2 | | 474845.9 | | |
| 1 | 0.5 | 465193.4 | 466118.30 | 97 |
| 2 | | 467043.2 | | |
| 1 | 1 | 437761.3 | 441128.25 | 92 |
| 2 | | 444495.2 | | |
| 1 | 3 | 357474.9 | 340127.95 | 71 |
| 2 | | 322781.0 | | |
| 1 | 6 | 255851.7 | 248801.25 | 52 |
| 2 | | 241750.8 | | |
| 1 | 8 | 204171.0 | 199693.60 | 42 |
| 2 | | 195216.2 | | |
| 1 | 24 | 33754.0 | 35358.65 | 7 |
| 2 | | 36963.3 | | |
| 1 | 48 | 2719.8 | 2755.10 | 1 |
| 2 | | 2790.4 | | |

Blood Stability Results for 2250 in Presence of 2244

| | 2250 into 2244 at 37° C. | | | |
|---|---|---|---|---|
| QC | Time (h) | Area | Mean | % Stability |
| 1 | 0 | 104556.2 | 106507.05 | 100 |
| 2 | | 108457.9 | | |
| 1 | 0.5 | 100166.7 | 101522.30 | 95 |
| 2 | | 102877.9 | | |
| 1 | 1 | 99813.3 | 100435.60 | 94 |
| 2 | | 101057.9 | | |
| 1 | 3 | 64110.6 | 67688.05 | 64 |
| 2 | | 71265.5 | | |
| 1 | 6 | 46378.1 | 46008.05 | 43 |
| 2 | | 45638.0 | | |
| 1 | 8 | 32608.4 | 34176.60 | 32 |
| 2 | | 35744.8 | | |
| 1 | 24 | 2973.3 | 2824.30 | 3 |
| 2 | | 2675.3 | | |
| 1 | 48 | 21.8 | 24.90 | 0 |
| 2 | | 28.0 | | |

The results unexpectedly demonstrated that compounds 2289 and 2293 has a very similar profile human blood stability to 2250 in that they metabolize or degrade within about 20-25 minutes into 2250, which shows a similar stability profile to the experiment conducted with 2250:

| 2289 into 2250 and 2244 at 37° C. | | | | |
|---|---|---|---|---|
| QC | Time (h) | Area | Mean | % Stability |
| 1 | 0 | No peak | No peak | Not stable- |
| 2 | | No peak | | converted to 2250 |
| 1 | 0.25 | No peak | No peak | NA |
| 2 | | No peak | | |
| 1 | 0.5 | No peak | No peak | NA |
| 2 | | No peak | | |
| 1 | 1 | No peak | No peak | NA |
| 2 | | No peak | | |
| 1 | 6 | No peak | No peak | NA |
| 2 | | No peak | | |
| 1 | 8 | No peak | No peak | NA |
| 2 | | No peak | | |
| 1 | 24 | No peak | No peak | NA |
| 2 | | No peak | | |
| 1 | 48 | No peak | No peak | NA |
| 2 | | No peak | | |

| 2250 (from 2289) into 2244 at 37° C. | | | | |
|---|---|---|---|---|
| QC | Time (h) | Area | Mean | % Stability |
| 1 | 0 | 110791.7 | 107230.25 | 100 |
| 2 | | 103668.8 | | |
| 1 | 0.25 | 102401.4 | 97129.65 | 91 |
| 2 | | 91857.9 | | |
| 1 | 0.5 | 100264.6 | 103079.35 | 96 |
| 2 | | 105894.1 | | |
| 1 | 1 | 96383.0 | 92960.90 | 87 |
| 2 | | 89538.8 | | |
| 1 | 6 | 46388.0 | 45423.85 | 42 |
| 2 | | 44459.7 | | |
| 1 | 8 | 31062.5 | 31429.45 | 29 |
| 2 | | 31796.4 | | |
| 1 | 24 | 2523.0 | 2587.00 | 2 |
| 2 | | 2651.0 | | |
| 1 | 48 | 40.8 | 49.15 | 0 |
| 2 | | 57.5 | | |

| 2293 into 2250 and 2244 at 37° C. | | | | |
|---|---|---|---|---|
| QC | Time (h) | Area | Mean | % Stability |
| 1 | 0 | No peak | No peak | Not stable- |
| 2 | | No peak | | converted to 2250 |
| 1 | 0.25 | No peak | No peak | NA |
| 2 | | No peak | | |
| 1 | 0.5 | No peak | No peak | NA |
| 2 | | No peak | | |
| 1 | 1 | No peak | No peak | NA |
| 2 | | No peak | | |
| 1 | 6 | No peak | No peak | NA |
| 2 | | No peak | | |
| 1 | 8 | No peak | No peak | NA |
| 2 | | No peak | | |
| 1 | 24 | No peak | No peak | NA |
| 2 | | No peak | | |
| 1 | 48 | No peak | No peak | NA |
| 2 | | No peak | | |

| 2250 (from 2293) into 2244 at 37° C. | | | | |
|---|---|---|---|---|
| QC | Time (h) | Area | Mean | % Stability |
| 1 | 0 | 98045.8 | 96716.40 | 100 |
| 2 | | 95387.0 | | |
| 1 | 0.25 | 93443.9 | 95622.90 | 99 |
| 2 | | 97801.9 | | |
| 1 | 0.5 | 96124.9 | 94573.25 | 98 |
| 2 | | 93021.6 | | |
| 1 | 1 | 86856.8 | 88083.70 | 91 |
| 2 | | 89310.6 | | |
| 1 | 6 | 41523.7 | 42680.45 | 44 |
| 2 | | 43837.2 | | |
| 1 | 8 | 30965.5 | 30788.65 | 32 |
| 2 | | 30611.8 | | |
| 1 | 24 | 2722.0 | 2679.95 | 3 |
| 2 | | 2637.9 | | |
| 1 | 48 | 0.0 | 0.00 | 0 |
| 2 | | 0.0 | | |

The half-life of each of compounds 2296 and 2289 and 2293 (through metabolization to 2250) is significantly higher than the half-life of taurolidine.

While the subject matter of this disclosure has been described and shown in considerable detail with reference to certain illustrative examples, including various combinations and sub-combinations of features, those skilled in the art will readily appreciate other aspects and variations and modifications thereof as encompassed within the scope of the present disclosure. Moreover, the descriptions of such aspects, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. A compound selected from:

a compound of Formula I:

Formula I

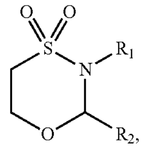

wherein $R_1$ is —CO-aryl and $R_2$ is H;

2289

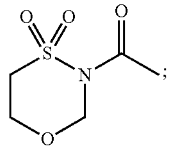

; or

2293

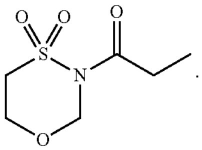

.

2. A pharmaceutical composition comprising at least one compound of claim 1 and a pharmaceutically acceptable carrier.

3. The pharmaceutical composition of claim 2, wherein said composition is in the form of an orally administrable composition.

4. The pharmaceutical composition of claim 2, wherein said composition is in the form of a capsule, a tablet, or a pharmaceutically acceptable solution.

5. The pharmaceutical composition of claim 2, wherein said composition contains the compound at a concentration of about 0.01 to about 3% w/v.

6. The pharmaceutical composition of claim 2, wherein said composition contains the compound at a concentration of about 0.01 to about 1000 μg/ml.

7. The pharmaceutical composition of claim 2, wherein said composition contains one or more solubilizing agents.

8. The pharmaceutical composition of claim 2, wherein said composition comprises a polyol.

9. The pharmaceutical composition of claim 2, wherein said composition is an injection and/or infusion formulation comprising a pharmaceutically acceptable injection or infusion carrier.

10. An oral dosage form comprising at least one compound of claim 1.

11. A method of treating a subject suffering from cancer comprising administering to said subject the compound of claim 1.

12. The method of claim 11, wherein the cancer is glioblastoma, glioma, neuroblastoma, astrocytoma, carcinomatous meningitis, colon cancer, rectal cancer, colorectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, leukemia, lymphoma, lymphosarcoma, adenocarcinoma, fibrosarcoma, or a metastasis thereof.

13. A method of treating a subject suffering from a microbial infection comprising administering to said subject the compound of claim 1.

14. A method of treating tumor stem cells in a subject comprising administering to said subject the compound of claim 1.

15. A method of treating a subject in need of anti-angiogenesis comprising administering to said subject the compound of claim 1.

16. A method of treating a subject in need of anti-tubulogenesis comprising administering to said subject the compound of claim 1.

17. A method of treating a subject suffering from a bacterial infection comprising administering to said subject the compound of claim 1.

18. A method of treating a subject suffering from a viral infection comprising administering to said subject the compound of claim 1.

19. A method of providing a co-therapeutic regimen to a subject, comprising administering taurolidine and/or taurultam in combination with at least one compound of claim 1, as a co-therapy to the subject.

20. The method of claim 19, wherein said method comprises administering a dosage of 0.1-1,000 mg/kg of said at least one compound in combination with a dosage of 0.01-500 mg/kg of taurolidine and/or taurultam.

21. The method of claim 19, wherein said method comprises administering a total daily dose of about 0.1 g to about 100 g of said at least one compound in combination with a total daily dose of about 0.01 g to about 50 g of taurolidine and/or taurultam.

22. A method of broadening the pharmacokinetic effects of taurolidine and/or taurultam in a human subject using at least two compounds having different half-lives, comprising administering to the human subject taurolidine and/or taurultam in combination with at least one compound of claim 1.

23. A method of providing a co-therapeutic regimen to a subject, comprising administering a) at least one compound of claim 1, as a co-therapy to the subject with b) carmustine, cytarabine, gemcitabine, nabPaclitaxel, asparaginase, procarbazine, mitomycin, 5-FU, methotrexate, vinblastine, dacarbazine, cisplatin, carboplatin, paclitaxel, bevacizumab, one or more checkpoint inhibitors, one or more PARP inhibitors, one or more anti-PD-1 drugs, docetaxel, irinotecan, doxorubicin, erlotinib, olaparib, lapatinib, topotecan, capecitabine, oxaliplatin, cyclophosphamide, ifosfamide, or a combination thereof.

* * * * *